US012193436B2

(12) United States Patent
Jendrisak (10) Patent No.: US 12,193,436 B2
(45) Date of Patent: Jan. 14, 2025

(54) APPARATUS AND METHODS FOR DELIVERING COLD PERFUSION FLUIDS IN ORGAN DONORS

(71) Applicant: Martin Jendrisak, Elgin, IL (US)

(72) Inventor: Martin Jendrisak, Elgin, IL (US)

(73) Assignee: Gift of Hope Organ & Tissue Donor Network, Itasca, IL (US)

( * ) Notice: Subject to any disclaimer, the term of this patent is extended or adjusted under 35 U.S.C. 154(b) by 329 days.

(21) Appl. No.: 17/893,378

(22) Filed: Aug. 23, 2022

(65) Prior Publication Data

US 2022/0400666 A1 Dec. 22, 2022

Related U.S. Application Data

(62) Division of application No. 16/201,368, filed on Nov. 27, 2018, now Pat. No. 11,439,144.

(51) Int. Cl.
*A01N 1/02* (2006.01)
*A61B 17/34* (2006.01)
*A61F 7/12* (2006.01)
*A61M 25/00* (2006.01)

(52) U.S. Cl.
CPC ........ *A01N 1/0247* (2013.01); *A61B 17/3421* (2013.01); *A61F 7/12* (2013.01); *A61M 25/00* (2013.01); *A61M 25/0097* (2013.01); *A61F 2007/126* (2013.01)

(58) Field of Classification Search
CPC ... A01N 1/0247; A61F 2007/126; A61F 7/12; A61M 25/0097
See application file for complete search history.

(56) References Cited

U.S. PATENT DOCUMENTS

| 5,221,258 | A | 6/1993 | Shturman |
| 6,508,777 | B1 | 1/2003 | Macoviak |
| 6,589,206 | B1 | 7/2003 | Sharkawy |
| 2001/0010247 | A1 | 8/2001 | Snow |
| 2004/0158208 | A1 | 8/2004 | Jeijima |

FOREIGN PATENT DOCUMENTS

ES 1196087 U 10/2017

OTHER PUBLICATIONS

PCT International Search Report and Written Opinion dated Feb. 3, 2020 in corresponding PCT Application No. PCT/US19/62113.

*Primary Examiner* — Deanna K Hall
(74) *Attorney, Agent, or Firm* — Vitale, Vickrey, Niro, Solon & Gasey LLP

(57) ABSTRACT

The present disclosure relates to devices and methods for increasing the probability of a successful organ donation by decreasing organs' warm ischemia time. Furthermore, the present disclosure relates to increasing the pool of eligible donors, including donors who had prior chest surgeries or prior abdominal surgeries. The present disclosure provides a catheter extending through a cannula, wherein the cannula delivers cold perfusion fluid and the catheter blocks the aorta, forcing the cold perfusion fluid to pass to organs in the donor's abdomen. The present disclosure further provides for advancing the catheter from a retracted position to an extended position, and creating a watertight seal at the cannula to prevent backflow of cold perfusion fluid.

6 Claims, 6 Drawing Sheets

APPARATUS AND METHODS FOR DELIVERING COLD PERFUSION FLUIDS IN ORGAN DONORS

This application is a divisional of and claims priority to U.S. application Ser. No. 16/201,368, filed on Nov. 27, 2018, presently pending, which is incorporated herein in its entirety by reference.

FIELD OF THE INVENTIONS

The present inventions relate to the field of organ donation, and more specifically, to devices and methods for more quickly achieving endovascular control and more quickly introducing cold profusion fluid to the organs, thereby improving the probability of successfully removing viable organs for transplanting.

DESCRIPTION OF RELATED ART

In the field of organ donations, it is critical that organs be flushed and surgically recovered quickly, because organ-viability progressively deteriorates upon cessation of blood flow and said organs expire quickly—especially at warm temperatures. A key to preserving the viability of transplantation is the rapid, in-situ organ perfusion with specifically formulated cold preservation solution. Organs are preferably cooled to near 0° C., as quickly as possible. Organs should not be allowed to remain at body temperature after blood flow stops. This is referred to as warm ischemia time, or WIT in short. Also important to transplant success is to keep the time between cold storage of a donated organ and the re-establishment of circulation after transplantation. This interval is termed cold ischemia time, or CIT and is managed by expediting surgical implantation.

Organ donations from deceased donors occurs in one of two scenarios. The first is a "donation after brain death" situation, also referred to as DBD. In DBD, organs are donated after a donor has been declared brain dead. In this DBD scenario, circulation and oxygenation in the donor are supported by ICU level of care, including mechanical ventilation, throughout the donation processes, including during surgical dissection in the operating room.

A second scenario is donation after circulatory death, or DCD in short. In a DCD setting, a donor's family has decided to discontinue futile resuscitation efforts and transition to providing end of life comfort care. To accommodate wishes for organ donation to occur, preparations are made for expedited organ procurement following circulatory arrest and a declaration of death. Organs currently eligible for DCD recovery include lungs, liver, pancreas, and kidneys. Inherent in the DCD process is an unpredictable period of organ WIT due to reduced blood circulation and oxygen delivery throughout the body prior to death. The only measure to limit WIT to the abdominal organs (liver, pancreas and kidneys) in the DCD setting is to institute in-situ cold perfusion, as quickly as possible, through the abdominal aorta. This is a formidable technical challenge as the prior art methods apply a conventional surgical approach.

More specifically, the prior art methods include introducing cold perfusion fluid through a cannula inserted into the distal portion of the abdominal aorta and institute infusion of the cold preservation solution. Then, it is necessary to compress, or "cross clamp," the aorta with a vascular clamp at or above the diaphragm in-order-to restrict flow of the cold perfusion fluid to the abdominal organs which derive their blood supply from the abdominal aorta. In the absence of a cross clamp, much cold perfusion fluid would be lost to the upper body and thus loss of cold perfusion fluid needed for the abdominal organ preservation. Achieving rapid upper abdominal aorta cross clamp application is technically challenging and time consuming in the DCD setting which contributes to increased WIT and risk to organ viability. Therefore, the preferred prior art techniques is to divide the sternum, enter the left chest cavity and expose the descending thoracic aorta for vascular cross clamp application. Although a second surgeon to perform thoracic aorta cross clamp would help minimize WIT, availability of two surgeons is generally unlikely and thus not a practical solution.

The prior art techniques have many disadvantages. For example, the process of dividing the sternum to achieve cross clamping can be time consuming and leave organs exposed to warmer temperatures. Moreover, if a donor had prior open heart surgery, the sternum is likely closed with wires, which completely precludes the ability to divide the sternum and achieve cross clamping in a timely manner. Similarly, a donor with prior left chest surgery, or infections, may have scarring, which again impedes rapid access to the aorta in the chest.

Yet another disadvantage of the prior art is that a donor's prior abdominal surgery poses a barrier to DCD organ donation. This is because, after an abdominal surgery, adhesions form inside the abdominal cavity. These adhesions can be extensive and require careful, time-consuming surgical dissection in-order-to gain access to the aorta and abdominal organs. Prior art techniques do not address this clinical scenario.

Therefore, it would be advantageous to achieve rapid proximal aorta occlusion without requiring a surgeon to divide the sternum, and without the need for surgical exposure as required by the prior art methods and devices. It would also be advantageous for overcome a donor's prior abdominal surgery in DCD organ donation.

BRIEF SUMMARY OF THE INVENTIONS

The inventions include devices and methods for achieving endovascular control and delivering cold perfusion fluid in an organ donor. The inventions provide numerous advantages over the prior art, as will become apparent from the present disclosure.

For example, some embodiments include a catheter inserted through a cannula. The cannula may have a proximal and a distal end, wherein the proximal end is attached to a y-connect having a first branch and a second branch. The y-connect and the cannula are optionally unitarily formed. Cold perfusion fluid may be delivered through the first branch. A rubber stop may be mounted to the second branch. A catheter may be inserted through the second branch and into the cannula. The catheter may comprise an inflatable balloon, a hub, a balloon port, and a distal port. In some embodiments, a syringe is attached to the balloon port, through a stopcock. The catheter may have a retracted position, in which the balloon is deflated and positioned inside the distal end of the cannula. The catheter may be configured to advance a predetermined distance beyond the proximal end of the cannula, to an extended position. The extended position may be 20 cm beyond the retracted position. In the extended position, the balloon may be inflated to block a donor's aorta.

The inventions also contemplate novel methods. For example, in some embodiments, a cannula may be inserted into a donor's distal abdominal aorta, wherein the cannula has a distal end and a proximal end, the proximal end is split into a first branch and a second branch, and a catheter extends through the second branch into the cannula's distal end. Cold perfusion fluid may be delivered through the first branch. The catheter may be advanced a predetermined distance beyond the cannula's distal end to an extended position. The balloon may be inflated once the catheter reaches its extended position. A watertight seal may be created to prevent the backflow of cold perfusion fluid by press-fitting a hub on the catheter into a rubber stop on the second branch.

Therefore, it is an object of the present inventions to provide improved apparatuses and methods for rapidly achieving endovascular control. It is a further object of the inventions to deliver cold perfusion fluid through a cannula and to a donor's aorta. Further yet, it is an object of the inventions to reduce warm ischemia time, and therefore increase the likelihood of a successful transplant.

Additionally, objects of the invention include eliminating the need to divide a donor's sternum to control the donor's aorta. In some embodiments, the it is an object of the inventions to enable the recovery of organs from donors who had prior chest surgery or abdominal surgery and are thus not eligible donors under prior art techniques.

DETAILED DESCRIPTION OF THE PREFERRED EMBODIMENTS

Before any embodiments of the invention are explained in detail, it is to be understood that the inventions are not limited in their application to the details of construction and/or arrangement of components set forth in the following description or illustrated in the following drawings. The invention is capable of other embodiments and of being practice or being carried out in various ways. Also, it is to be understood that the phraseology and terminology used herein for the purpose of this description should not be regarded as limiting.

The following discussion is presented to enable a person skilled in the art to make and use embodiments of the invention. Various modifications to the illustrated embodiment will be readily apparent to those skill in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which the elements in different figures have like reference numerals. The figures, which are not necessarily to scale, depict selected embodiments and are not intended to limit the scope of embodiments of the invention. A person having ordinary skill in the art will recognize the exampled provided herein have many useful alternatives and fall within the scope of embodiments of the invention.

The present disclosure is generally directed to an apparatus and method for achieving rapid delivery of cold perfusion fluid and endovascular control (i.e., effectively "cross-clamping" the proximal aorta). The inventions more quickly deliver cold perfusion fluid, thereby decreasing warm ischemia time. The result is improved probability of a successful organ donation and transplant. As will become apparent from the following description, the invention includes both embodiments of an apparatus, methods of using the apparatus, and methods of achieving endovascular control while delivering cold perfusion fluid.

Generally speaking, the inventions may include an aorta cannula 110 which delivers cold perfusion fluid through a donor's aorta, and through which a catheter 130 is advanced. For this reason, embodiments of inventions may be referred to as a "regional aortic perfusion cannula."

Figure 1:
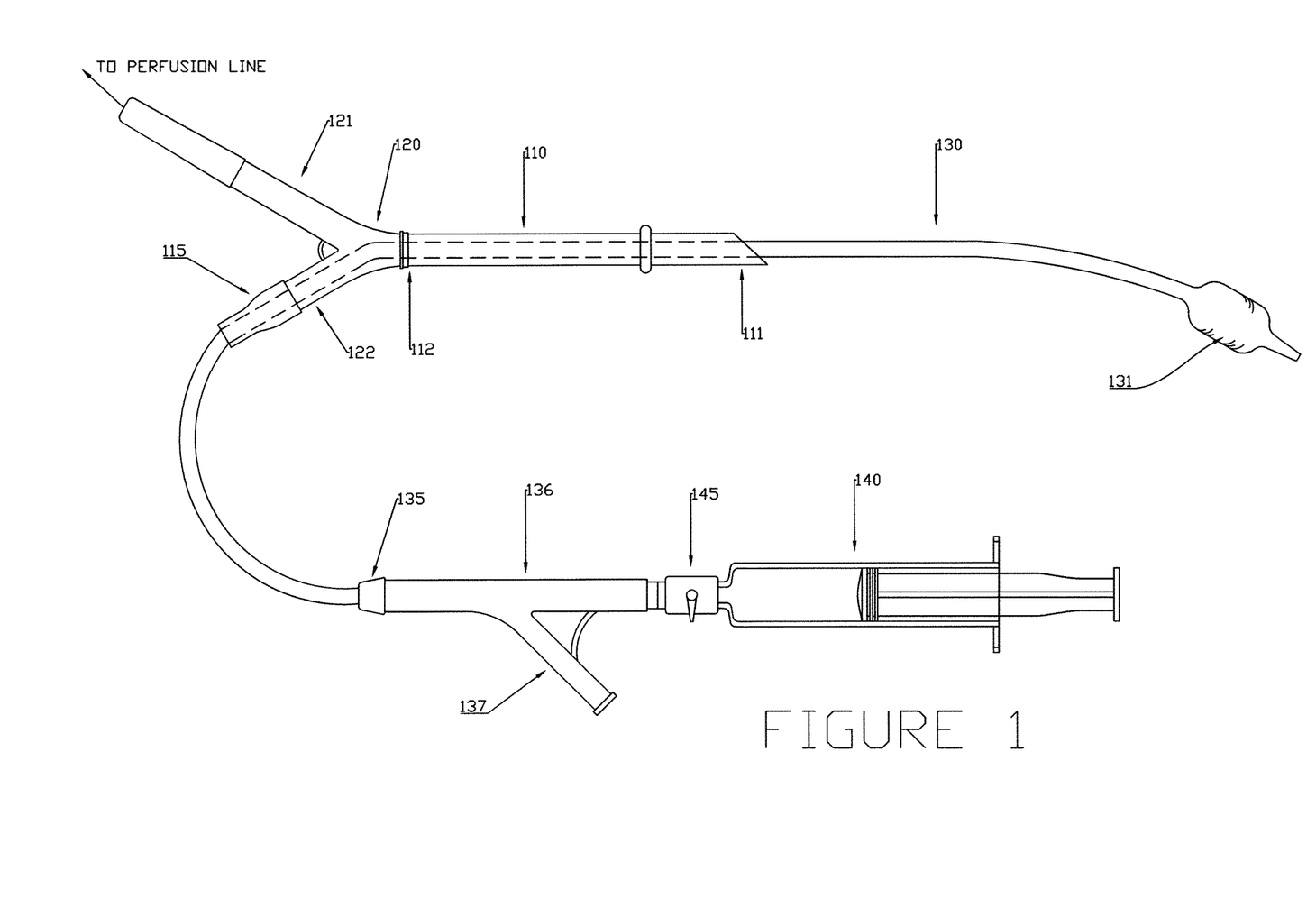
FIG. 1 is an embodiment of the present inventions.

Turning first to FIG. 1, the inventions may include an aorta cannula 110 which is constructed from a length of plastic tubing configured with a gradual taper. In some embodiments, the cannula 110 has a smaller, distal end 111 which is approximately 24 French in caliber, and thus ideally suited for insertion into the terminal end of the abdominal aorta. The proximal end 112 may be fastened to a y-connector 120. Although y-connector 120 is shown fastened to cannula 110, it should be understood that the present inventions also contemplate an embodiment wherein cannula 110 and y-connector 120 are unitarily formed, for example, using an injection molding process, or any other method of manufacturing known in the art.

In turn, y-connector 120 may have a first branch 121 and a second branch 122. Preferably, first branch 121 of y-connector 120 may be attached to a perfusion line, as known in the art. For example, such perfusion line may be configured with a drip chamber into which two short tubing lines with the free ends are affixed with plastic spikes for insertion into the perfusate storage bags under sterile conditions. Thus, cold perfusion fluid is delivered via the first branch 121 and through cannula 110.

Figure 3:
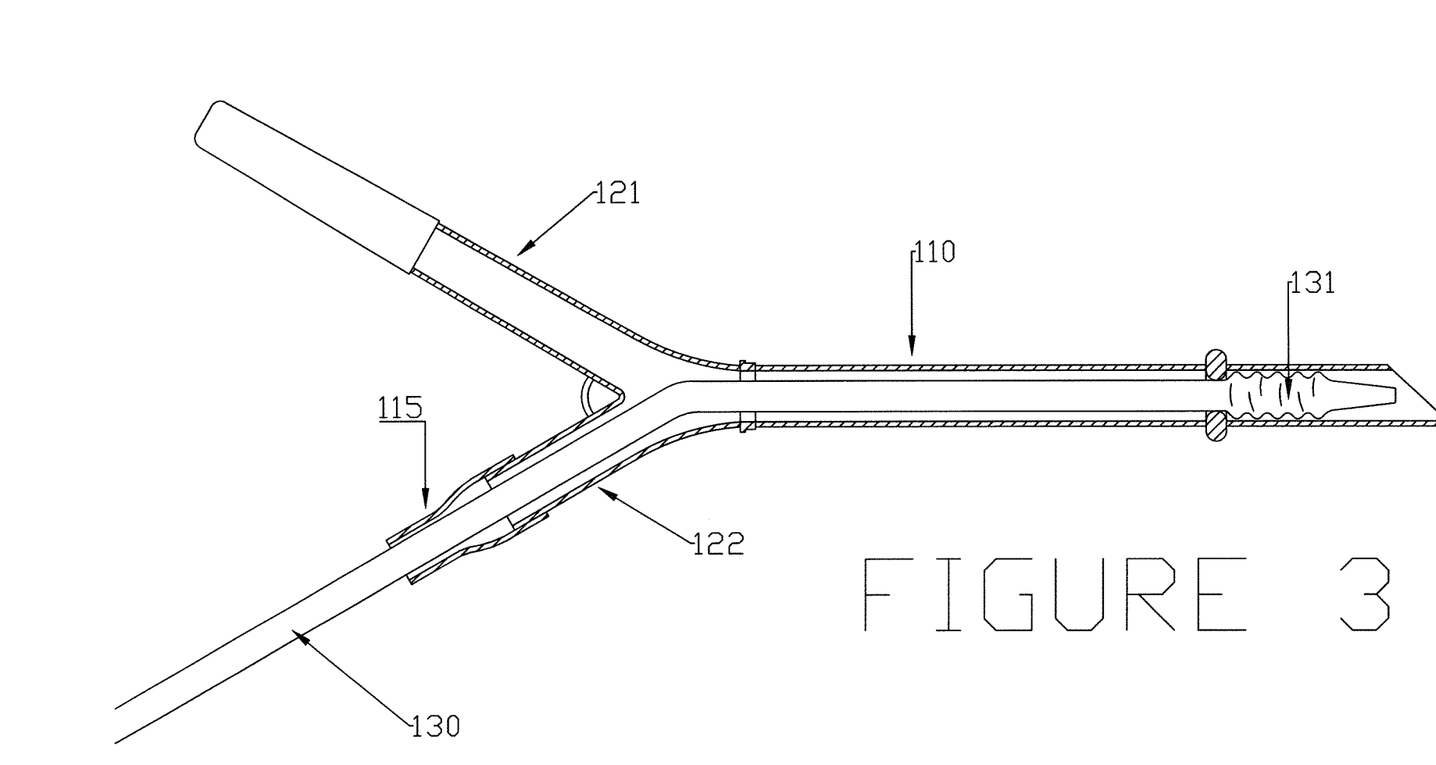
FIG. 3 is an embodiment of the present inventions, wherein a catheter is shown in a retracted position.
Figure 4A:
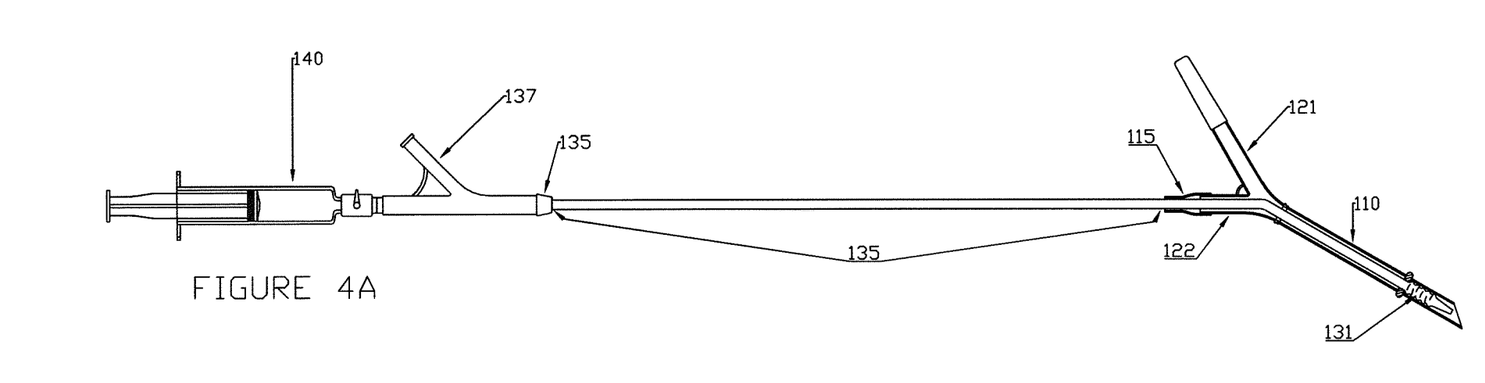
FIG. 4A is an embodiment of the present inventions, wherein a catheter is shown in a retracted position.

Turning to the second branch 122, embodiments of the invention provide an endovascular balloon catheter 130 which may be advanced through cannula 110. As will become apparent from the present disclosure, catheter 130 is advanced through an insertion point in the donor. Catheter 130 may be advanced from a first, retracted position, (seen for example in FIGS. 3 and 4A), to a second, extended position (seen for example in FIG. 4B). In the retracted position, balloon 131 is shown to be inside the distal tip of cannula 110. To reach the extended position, catheter 130 is advanced by a predetermined distance. In some embodiments, such a predetermined distance may be the length of the catheter 130 which extends beyond the proximal end of cannula 110. For example, FIG. 4A shows a catheter with a length extending a predetermined distance 135 beyond cannula 110. Moreover, in some embodiments of the inventions, such predetermined distance 135 is 20 cm. This exemplary predetermined length is selected because it is a common length between the donor's distal abdominal aorta (i.e., just above the iliac artery bifurcation) and the thoracic aorta. As will become apparent from the present disclosure, some embodiments of the present inventions include the advancement of a catheter from the distal abdominal aorta to the thoracic aorta (or, vice versa) and therefore 20 cm advancement is preferable. However, it should be noted that this distance is disclosed only for exemplary purposes, and the inventions may work equally well if other lengths are chosen.

In some embodiments, the catheter 130 is a balloon occlusion catheter (having a balloon 131) with approximately 7 French in caliber. Moreover, the catheter 130 has sufficient length to advance from a retracted position to an extended position. The extended position corresponds to proper balloon placement as it is advanced through the donor. Catheter 130 may include a balloon port 136 and a distal port 137. It should be understood that the balloon port 136 extends along the length of catheter 130 and is in fluid communication with the interior of balloon 131. The distal port 137 may similarly be in fluid communication with the tip of catheter 130.

A syringe 140 may be connected (through an optional stopcock 145) to the balloon port 136, and/or to the distal port 137. A person of ordinary skill in the art would recognize that the balloon port allows the inflation of balloon 131, for example by injecting saline through the balloon port 136. Likewise, a syringe connected to distal port 137 may draw or deliver fluid through the tip of catheter 130. As disclosed further herein, a syringe 140 connected to balloon port 136 may be used to inflate balloon 131 once catheter 130 is advanced and reaches its extended position.

Returning to FIG. 1, for example, the second branch 122 may have a diameter sufficiently large to permit introduction and advancement of an endovascular balloon catheter 130 into cannula 110 without obstructing perfusate flow. That is to say, a person of skill in the art would recognize that the diameter may vary, but it must be relatively large enough to permit introduction and advancement of catheter 130 without blocking the flow of cold perfusion fluid through cannula 110. In this way, catheter 130 extends through the second branch 122 and through cannula 110. As a result, catheter 130 can be advanced through cannula 110 and into its extended position according to the methods disclosed herein. Initiating the flow of cold perfusion fluid through cannula 110 helps to propel catheter 130 to its extended position.

Figure 2:
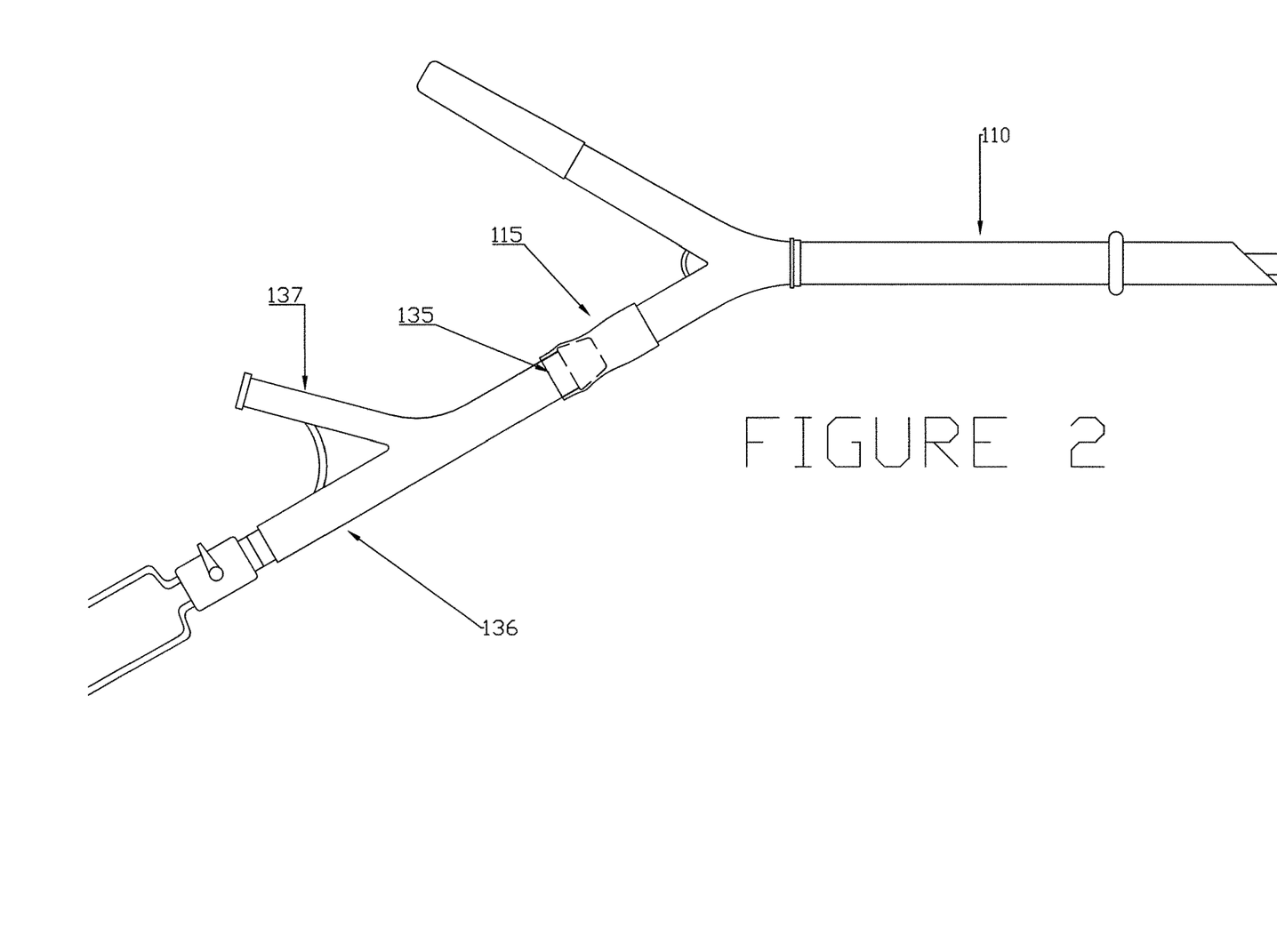
FIG. 2 is an embodiment of the present inventions, showing a press-fit between a catheter's hub and a rubber stop on a cannula.

Moreover, in some embodiments, a short silicon rubber sleeve may be fastened to the end of the second branch 122 of the y-connector 120, as seen for example in FIG. 2. The short silicon rubber sleeve acts as a stop 115 which can be engaged (by press-fit) with a hub 135 of the catheter 130 to form a watertight seal. In some embodiments of the inventions, catheter 130 extends approximately 20 cm beyond cannula 110. Thus, (as described further with respect to the method for using the inventions, below), after catheter 130 is advanced by 20 cms, its hub 135 engages the rubber stop 115 and forms a watertight seal. An example can be seen in FIG. 2, wherein catheter 130 is shown in its advanced position, and thus hub 135 has engaged the rubber stop. Hub 135 can be press-fit into the rubber stop 115 to ensure the seal is tight.

The watertight seal formed by press-fitting hub 135 into the rubber stop 115 serves to prevent the backflow of cold perfusion fluid, which is administered through the cannula 110 via the first branch 121 of the y-connector 120. That is to say, in the absence of the watertight seal formed by the engagement of hub 135 with the rubber stop, the cold perfusion fluid could flow back and out the second branch 122 through which the catheter 130 is being advanced.

A person of skill in the art would understand that a watertight seal can be also be created using components other than the hub 135 engaging the rubber stop. For example, in embodiments where the catheter extends more than 20 cm beyond cannula 110, hub 135 may be replaced, for example, by placing tape around catheter 130 at a predetermined position (for example, 20 cm) beyond cannula 110. In such an embodiment, the raised edge formed by the tape can be press-fit into the rubber stop 115, again forming a watertight seal.

Figure 5:
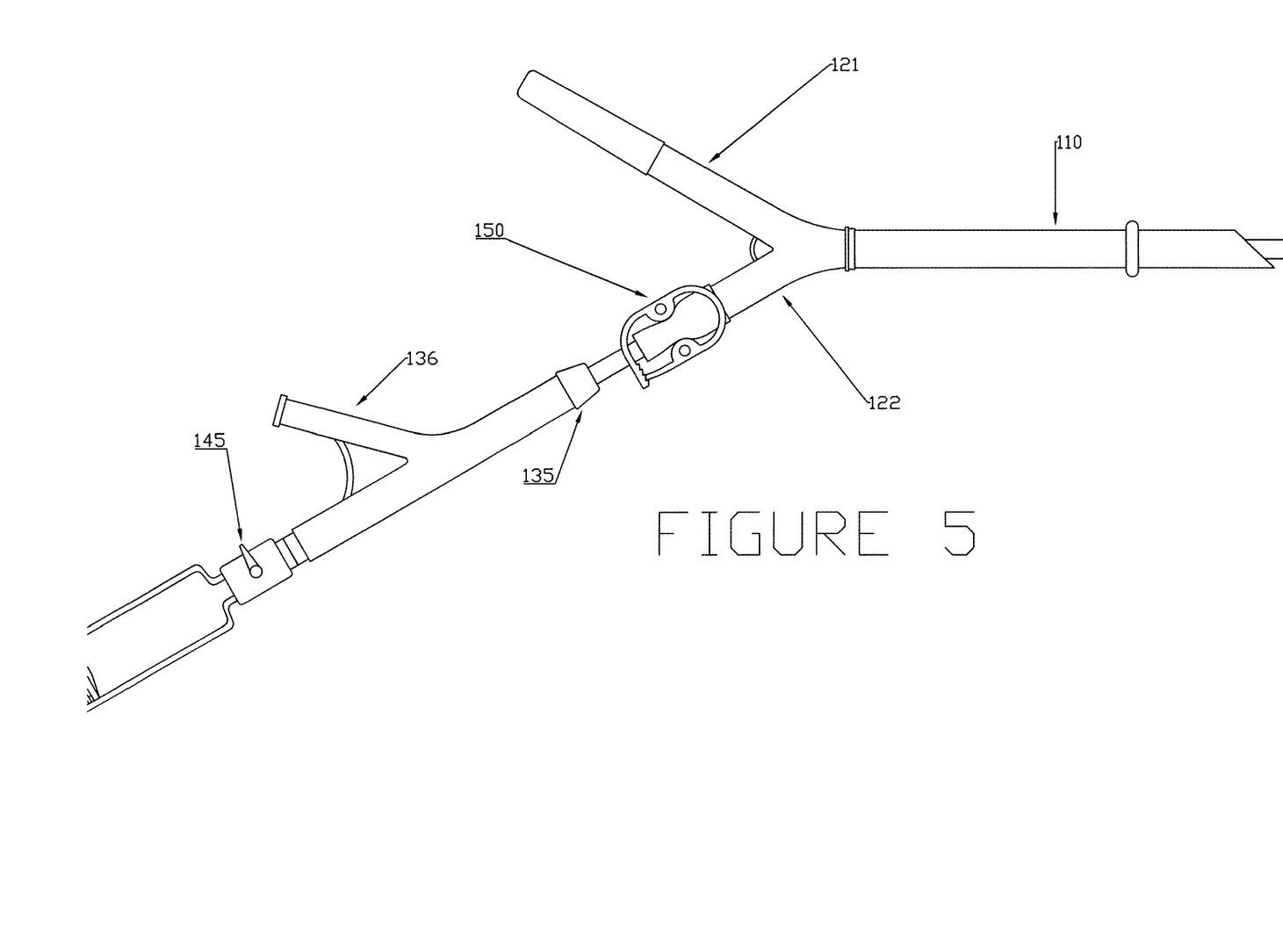
FIG. 5 shows an embodiment of the present inventions, wherein a line clamp seals a rubber stop to prevent backflow of perfusion fluid.

Furthermore, the present inventions also contemplate other components and methods for creating a watertight seal. For example, in some embodiments, a line clamp 150 is provided for clamping rubber stop 115 after the catheter 130 has been fully advanced. An example of line clamp 150 can be seen in FIG. 5. In some embodiments, line clamp 150 is provided in addition to hub 135. That is to say, some embodiments of the invention create a watertight seal by pressing hub 135 into rubber stop 115, and then closing line clamp 150. This acts as a redundant, belt-and-suspenders approach to ensuring that cold perfusion fluid does not flow back.

Further yet, a one-way value may be provided in addition to, or instead of, line clamp 150. In such embodiments, the one-way value would be closed once catheter 130 has been advanced to its extended position. Embodiments having a one-way valve or a line clamp 150 require the additional step of sealing/clamping after advancing the catheter 130. Thus, a surgeon must be mindful of taking an additional step to activate the watertight seal. Nonetheless, all arrangements and configurations are within the scope of the contemplated inventions.

The above-described apparatus, or a substantially similar apparatus, may be used to recover organs from a donor. The present inventions extend to methods and techniques for recovering organs from a donor. The present inventions provide the advantage of decreasing warm ischemia time, and also allow access to organs in donors who would otherwise be ineligible. For example, the inventions make it possible to recover organs from donors who had previous chest surgeries, and also from donors who have abdominal adhesions.

Figure 4B:
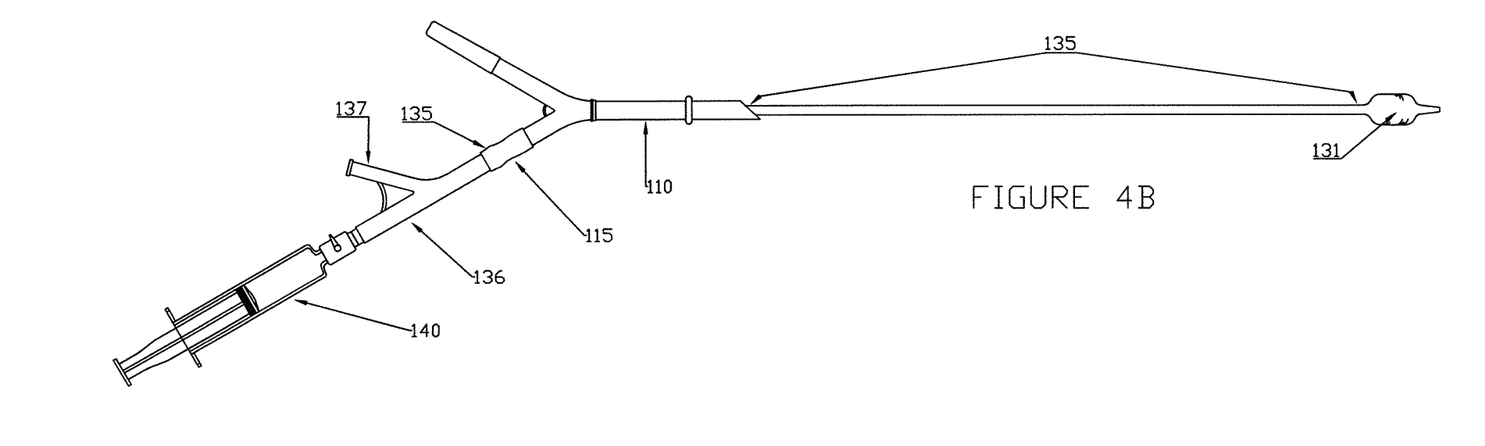
FIG. 4B is an embodiment of the present inventions, wherein a catheter is shown in an extended position.

In embodiments of the inventions, a cannula 110 is packed with a catheter 130, where the catheter 130 (with deflated balloon 131) is advanced to the distal tip of the cannula 110. An example of a deflated balloon 131, in its retracted position (inside cannula 110) is shown in FIG. 4A. Prior to inserting the cannula 110 into the donor, the catheter 130 may be tested by fully advancing it, as seen for example in FIG. 4B. In some embodiments, the catheter 130 may be advanced until its hub end 135 is press-fitted into a rubber stop 115 affixed to a second branch 122 of cannula 110. An example is seen in FIG. 4B, where catheter is advanced fully to its extended position and hub 135 is press-fitted into rubber stop 115. At this point, the balloon may be test filled and deflated by pushing a syringe 140 (via the balloon port 136) to inflate the balloon with saline, while leaving 25-30 cc in the syringe. The balloon 131 should inflate without leakage to confirm that no component has failed.

Catheter 130 is returned to its retracted position (with a deflated balloon 131) in the distal tip of the aortic cannula 110. A perfusion line is connected to the first branch 121, such that cold perfusion fluid can be delivered through cannula 110 and into the donor's aorta. The cannula 110 should be flushed with cold perfusate to expel air prior to usage.

After a donor's death declaration following the loss of circulation, rapid laparotomy and surgical exposure of the distal abdominal aorta is performed. In some embodiments of the inventions, the distal abdominal aorta becomes the incision point into which the distal end of cannula 110 is inserted. As a person of skill in the art would recognize, cannula 110 may be secured with a watertight ligature, or with a Babcock clamp (not shown).

Figure 6:
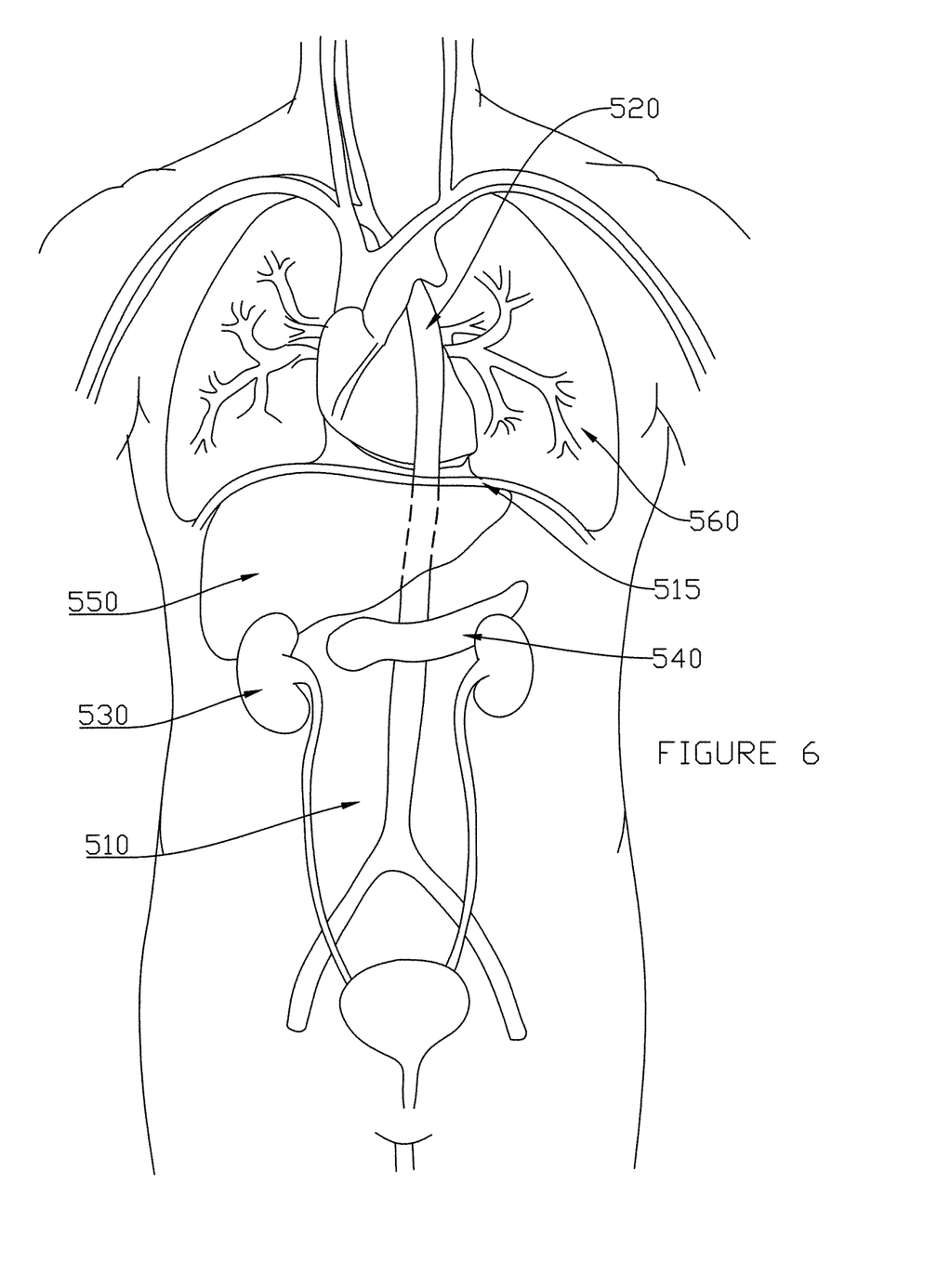
FIG. 6 is an anatomical diagram illustrating an exemplary cannula insertion point, and advancement of a catheter.

FIG. 6 provides context of how the methods of the present inventions may be used. First, cannula 110 may be inserted, for example into the distal abdominal aorta (see e.g. FIG. 6, reference number 510), and then the cold perfusion line is activated. Cold perfusion fluid is delivered, through first branch 121, through cannula 110, and into the donor's distal abdominal aorta 510. Moreover, catheter 130 is fully advanced. The flow of cold perfusion fluid may help to propel catheter 130. Applicant's testing indicates that, in most scenarios, advancing catheter 130 by 20 cms will position the catheter 130 in the thoracic aorta 520. In any event, it should be understood that balloon 131 should be advanced above the donor's diaphragm 515.

In some embodiments of the inventions, the catheter 130 has a hub 135 which engages a rubber stop 115 on the cannula 110, by press fit, when the catheter 130 is in its extended position. Thus, as catheter 130 reaches its extended position, a surgeon may press-fit hub 135 into stop 115 to create a watertight seal. In some embodiments of the invention, second branch 122 may be clamped using a line clamp 150, or a one-way valve may be shut to prevent the backflow of cold perfusion fluid.

Once fully extended, the balloon 131 is fully inflated with saline. Balloon 131 may be inflated using an attached syringe 140 with a stopcock 145 turned to a closed position. Inflating the balloon 131 blocks the proximal thoracic aorta 520. As such, cold perfusion fluid is not lost through the aorta (for example, to the donor's upper extremities) and is instead directed to the donor's organs for recovery. Blocking the aorta using a balloon may be referred to as achieving "endovascular control."

Cold perfusion fluid travels from the insertion point (in some embodiments, the distal abdominal aorta 510) up the aorta and to organs such as kidneys 530, pancreas 540, liver 550 and/or lungs 560. To ensure that the balloon 131 is properly placed and inflated, a surgeon may use syringe 140 to draw fluid through catheter 130's distal port 137. If the aorta is properly blocked, only blood (and no perfusion fluid) should be drawn. If perfusion fluid is drawn through distal port 137, then balloon 131 has not properly or sufficiently blocked the donor's aorta.

Moreover, the distal vena cava (adjacent to the exposed aorta 510 but not shown) may be immediately incised to vent the effluent. A person of ordinary skill in the art, with the benefit of the present disclosure, would recognize that venting is important to relieving pressure in the aorta (and in the organs) created by the introduction of the cold perfusion fluid. In other words, the cold perfusion fluid delivered via cannula 110 may travel to the donor's organs, flush them, and vent, or "drain," through an incision in the vena cava. Once flushed, organs are explanted (with or without sternotomy), quickly packed, preferably with ice to aid cooling, and immediately prepared for transplantation. For liver procurement, the inferior mesenteric vein is cannulated for delivery of cold perfusate into the portal circulation. The common bile duct is transected and gallbladder incised for early flush of the biliary tree. After completing the in-situ organ flush, the balloon may be deflated and the catheter 135 may be removed.

The present inventions deliver cold perfusion fluid faster, and block the proximal thoracic aorta faster, than prior art devices and methods. Accordingly, cold perfusion fluid is delivered to the organs faster, the organs are cooled faster, and the likelihood of a successful transplant is increased. Moreover, the prior art techniques require a surgeon to open a donor's chest to cross-clamp the aorta. The present inventions overcome this disadvantage, as they do not require a donor's sternum to be divided. Therefore, the present inventions have the additional advantage of allowing organ donations by donors who had previous chest surgeries.

The present inventions further include methods for recovering organs from donors who had prior abdominal surgery. Currently, such donors are excluded from DCD donation, because rapid abdominal aortic exposure and cannulation (as described, for example, above) is not possible in view of adhesions formed after prior surgery. Thus, embodiments of the present invention overcome the difficulty in achieving abdominal aortic exposure and cannulation by inserting cannula 110 into the thoracic aorta 520 in the chest, and advancing the balloon 131 distally toward the distal abdominal aorta 510. In that position, balloon 131 may be inflated. Stated more generally, contemplated embodiments of the invention include cannulating at the donor's chest and advancing the balloon distally. In this context, distally would be understood to mean anatomically downward, e.g. toward the donor's legs.

Generally speaking, for donors with prior abdominal surgery, the same steps are performed, except in such embodiments of the inventions, cannula 110 is inserted to the thoracic aorta in the chest and balloon 131 is inflated in the distal abdominal aorta 510. Again, a cold perfusion line is activated to deliver cold perfusate, and catheter 130 is advanced, this time distally towards the donor's legs. The catheter 130 is advanced to the distal abdominal aorta and balloon 131 is inflated via syringe 140. Once the catheter 130 reaches its extended position, the balloon is inflated to block the aorta. In this scenario, the balloon blocks cold perfusion fluid from being lost to the donor's legs. The blockage instead forces the cold perfusion fluid into the organs, thereby flushing them. Cannula 110's second branch 122 must be sealed after catheter 130 reaches its extended position. Second branch 122 may be sealed using a press-fit between hub 135 and the rubber stop 115, using the clamp 150, or by sealing a one-way valve (not shown).

Although the above described devices and methods are particularly suitable in the "donation after circulatory death" scenario, it should be understood that the present inventions are not limited to DCD. Even in other donation scenarios, such as donation after brain death, it remains critical to achieve rapid endovascular control, and to rapidly deliver cold perfusion fluid to eligible organs. Moreover, as described above, the present inventions overcome the prior art's short-comings with respect to donors who have had surgeries which make it difficult or impossible to divide the sternum or to expose the abdominal aorta. Therefore, a person of ordinary skill in the art, having the benefit of the present disclosure, would understand that the inventions are intended for use all possible donation scenarios.

What is claimed:

1. A method for achieving endovascular control and delivering cold perfusion fluid to an organ donor, comprising the steps of:
    inserting a cannula into a donor's distal abdominal aorta, wherein the cannula has a distal end and a proximal end, the proximal end is split into a first branch and a second branch, and a catheter extends through the second branch into the cannula's distal end;
    delivering cold perfusion fluid through the first branch;

advancing the catheter a predetermined distance beyond the cannula's distal end to an extended position;

inflating a balloon on a distal end of the catheter once the catheter reaches its extended position; and creating a watertight seal in the first branch by press-fitting a hub on the catheter into a rubber stop on the second branch.

2. The method of claim 1, wherein the catheter's extended position corresponds to the balloon being in the donor's thoracic aorta.

3. The method of claim 2, wherein the predetermined distance is 20 cm.

4. The method of claim 3, wherein the step of inflating the balloon further comprises the step of using a syringe connected to a catheter's balloon port to deliver a saline solution to the balloon.

5. The method of claim 4, further comprising the step of using a syringe to draw from the catheter's distal port to confirm the balloon has blocked the thoracic aorta.

6. The method of claim 5, further comprising the step of venting the cold perfusion fluid through the donor's vena cava with fluid delivered through the cannula.

* * * * *